(12) United States Patent
Yamamoto et al.

(10) Patent No.: US 11,406,350 B2
(45) Date of Patent: Aug. 9, 2022

(54) PHOTOACOUSTIC MEASUREMENT DEVICE

(71) Applicant: FUJIFILM Corporation, Tokyo (JP)

(72) Inventors: Katsuya Yamamoto, Kanagawa (JP); Kaku Irisawa, Kanagawa (JP); Dai Murakoshi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 393 days.

(21) Appl. No.: 16/359,803

(22) Filed: Mar. 20, 2019

(65) Prior Publication Data

US 2019/0216424 A1 Jul. 18, 2019

Related U.S. Application Data

(63) Continuation of application No. PCT/JP2017/033342, filed on Sep. 14, 2017.

(30) Foreign Application Priority Data

Sep. 21, 2016 (JP) .............................. JP2016-183784

(51) Int. Cl.
*A61B 8/08* (2006.01)
*G01S 7/52* (2006.01)
(Continued)

(52) U.S. Cl.
CPC .......... *A61B 8/0841* (2013.01); *A61B 5/0095* (2013.01); *A61B 5/061* (2013.01);
(Continued)

(58) Field of Classification Search
CPC . A61B 5/0093; A61B 5/0095; A61B 5/14503; A61B 8/0841; A61B 8/488;
(Continued)

(56) References Cited

U.S. PATENT DOCUMENTS

2006/0247521 A1* 11/2006 McGee ................ A61B 5/0071
600/434
2011/0112778 A1* 5/2011 Lee ..................... G01S 7/52084
702/56
(Continued)

FOREIGN PATENT DOCUMENTS

JP 2009-207588 A 9/2009
JP 2013-226335 A 11/2013
(Continued)

OTHER PUBLICATIONS

Japanese Office Action, dated Nov. 12, 2019, for Japanese Application No. 2018-541023, along with an English translation.
(Continued)

*Primary Examiner* — Sean D Mattson
(74) *Attorney, Agent, or Firm* — Birch, Stewart, Kolasch & Birch, LLP

(57) ABSTRACT

Provided is a photoacoustic measurement device including: an ultrasound image generation unit that generates an ultrasound image on the basis of a detection signal of reflected ultrasonic waves generated by the transmission of ultrasonic waves; a puncture needle detection unit that detects a length direction of a puncture needle on the basis of the ultrasound image; and a controller that controls a steering direction of a sample gate which is a Doppler measurement target on the basis of the length direction of the puncture needle such that an angle θ formed between a straight line extending in the length direction of the puncture needle and a straight line extending in the steering direction of the sample gate satisfies 0°≤θ<90°.

13 Claims, 11 Drawing Sheets

(51) Int. Cl.
  *A61B 34/20* (2016.01)
  *G01S 15/89* (2006.01)
  *A61B 17/34* (2006.01)
  *A61B 5/00* (2006.01)
  *A61B 8/00* (2006.01)
  *A61B 5/06* (2006.01)
  *A61B 8/06* (2006.01)
  *A61B 90/00* (2016.01)
  *A61B 18/26* (2006.01)

(52) U.S. Cl.
  CPC .............. *A61B 8/469* (2013.01); *A61B 8/488* (2013.01); *A61B 8/54* (2013.01); *A61B 17/3403* (2013.01); *A61B 34/20* (2016.02); *G01S 7/52077* (2013.01); *G01S 7/52085* (2013.01); *G01S 15/8979* (2013.01); *A61B 8/06* (2013.01); *A61B 8/5223* (2013.01); *A61B 2017/3413* (2013.01); *A61B 2018/266* (2013.01); *A61B 2034/2063* (2016.02); *A61B 2034/2065* (2016.02); *A61B 2090/061* (2016.02); *A61B 2090/062* (2016.02); *A61B 2576/00* (2013.01)

(58) Field of Classification Search
  CPC ................ A61B 8/4245; A61B 8/5223; A61B 2017/3413; A61B 17/34; A61B 17/3403; A61B 2034/2063; A61B 2034/2065; A61B 90/13; A61B 34/20; A61B 5/4887; G01S 7/52085
  See application file for complete search history.

(56) References Cited

U.S. PATENT DOCUMENTS

| | | | | |
|---|---|---|---|---|
| 2012/0078103 | A1* | 3/2012 | Tashiro | A61B 8/54 600/443 |
| 2012/0253181 | A1* | 10/2012 | Okamura | A61B 8/5238 600/424 |
| 2013/0053687 | A1* | 2/2013 | Lin | A61B 8/13 600/424 |
| 2013/0096430 | A1* | 4/2013 | Yoshiara | A61B 8/463 600/438 |
| 2015/0094569 | A1* | 4/2015 | Ohuchi | A61B 8/0841 600/424 |
| 2015/0297092 | A1* | 10/2015 | Irisawa | A61B 8/12 600/407 |
| 2018/0125448 | A1* | 5/2018 | Karadayi | A61B 8/0841 |

FOREIGN PATENT DOCUMENTS

JP   2015-231583 A   12/2015
WO   WO-2013121743 A1 *   8/2013   ........... G01N 29/043

OTHER PUBLICATIONS

International Preliminary Report on Patentability and Written Opinion of the International Searching Authority (Forms PCT/IB/326, PCT/IB/373, and PCT/ISA/237) for International Application No. PCT/JP2017/033342, dated Apr. 4, 2019, with English translation.
International Search Report (Form PCT/ISA/210) for International Application No. PCT/JP2017/033342, dated Dec. 12, 2017, with English translation.

* cited by examiner

FIG. 8

| FRAME NUMBER | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| DETECTION PROCESS ON/OFF | ON | ON | OFF | ON | OFF | OFF | ON | OFF | OFF | OFF | ON | ON | ON | ON | OFF | ON | OFF | OFF | ON | OFF |
| ANGLE OF TRAVELING DIRECTION OF PUNCTURE NEEDLE | 30° | 30° | - | 30° | - | - | 30° | - | - | - | 45° | 20° | 15° | 15° | - | 15° | - | - | 15° | - |

PHOTOACOUSTIC MEASUREMENT DEVICE

CROSS-REFERENCE TO RELATED APPLICATIONS

This application is a continuation application of International Application No. PCT/JP2017/033342, filed Sep. 14, 2017, the disclosure of which is incorporated herein by reference in its entirety. Further, this application claims priority from Japanese Patent Application No. 2016-183784, filed Sep. 21, 2016, the disclosure of which is incorporated herein by reference in its entirety.

BACKGROUND OF THE INVENTION

1. Field of the Invention

The present invention relates to a photoacoustic measurement device comprising an insert of which at least a portion is inserted into a subject and which includes a photoacoustic wave generation portion that absorbs light and generates photoacoustic waves.

2. Description of the Related Art

An ultrasonography method has been known as a kind of image inspection method that can non-invasively inspect the internal state of a living body. In ultrasonography, an ultrasound probe that can transmit and receive ultrasonic waves is used. In a case in which the ultrasound probe transmits ultrasonic waves to a subject (living body), the ultrasonic waves travel in the living body and are reflected from the interface between tissues. The ultrasound probe receives the reflected ultrasonic waves and a distance is calculated on the basis of the time until the reflected ultrasonic waves return to the ultrasound probe. In this way, it is possible to capture an image indicating the internal aspect of the living body.

In addition, photoacoustic imaging has been known which captures the image of the inside of a living body using a photoacoustic effect. In general, in the photoacoustic imaging, the inside of the living body is irradiated with pulsed laser light. In the inside of the living body, a living body tissue absorbs the energy of the pulsed laser light and ultrasonic waves (photoacoustic waves) are generated by adiabatic expansion caused by the energy. For example, an ultrasound probe detects the photoacoustic waves and a photoacoustic image is formed on the basis of a detection signal. In this way, it is possible to visualize the inside of the living body on the basis of the photoacoustic waves.

In addition, as a technique related to the photoacoustic imaging, JP2015-231583A discloses a puncture needle in which a photoacoustic wave generation portion that absorbs light and generates photoacoustic waves is provided in the vicinity of a tip. In the puncture needle, an optical fiber is provided up to the tip of the puncture needle and light guided by the optical fiber is emitted to the photoacoustic wave generation portion. An ultrasound probe detects the photoacoustic waves generated by the photoacoustic wave generation portion and a photoacoustic image is generated on the basis of a detection signal of the photoacoustic waves. In the photoacoustic image, a part of the photoacoustic wave generation portion appears as a bright point, which makes it possible to check the position of the puncture needle using the photoacoustic image.

In addition, Doppler measurement has been known as a kind of ultrasonography. The Doppler measurement is a measurement method that non-invasively measures, for example, hemodynamics, a blood flow rate, and trends in vivo on the basis of the Doppler shift of the frequency of received waves with respect to the frequency of transmitted waves. For example, JP2009-207588A discloses a technique that detects the tip of a puncture needle in an ultrasound image and sets a sample gate as a Doppler measurement target in the vicinity of the tip, in order to easily check a blood flow on a puncture needle guide in a case in which Doppler measurement is performed while the puncture needle is being used.

SUMMARY OF THE INVENTION

Here, it is considered that the puncture needle generating photoacoustic waves disclosed in JP2015-231583A is used in order to check the position of the tip of the puncture needle in a case in which ultrasonography using the puncture needle is performed.

However, in a case in which Doppler measurement is performed using the puncture needle generating photoacoustic waves disclosed in JP2015-231583A, a Doppler signal obtained by the Doppler measurement is a weak signal. Therefore, in a case in which the relationship between an insertion direction of the puncture needle and a steering direction of the sample gate is not appropriately set, a signal caused by the reflected waves of the ultrasonic waves from the puncture needle is included as an artifact in the Doppler signal obtained by the Doppler measurement, which makes it difficult to acquire an accurate Doppler signal. Specifically, for example, as the angle formed between the insertion direction (length direction) of the puncture needle and the steering direction of the sample gate becomes closer to a right angle, the influence of the reflected waves from the puncture needle on the Doppler signal of the sample gate becomes larger.

In addition, JP2009-207588A does not disclose any technique considering the influence of the reflected waves from the puncture needle in a case in which a sample gate is set in the Doppler measurement.

The invention has been made in view of the above-mentioned problems and an object of the invention is to provide a photoacoustic measurement device that, in a case in which Doppler measurement is performed with an insert, such as a puncture needle that generates photoacoustic waves from a tip, can suppress the generation of an artifact caused by reflected waves from the insert.

According to the invention, there is provided a photoacoustic measurement device comprising: an insert of which at least a tip portion is inserted into a subject and which includes a light guide member that guides light to the tip portion and a photoacoustic wave generation portion that absorbs the light guided by the light guide member and generates photoacoustic waves; an acoustic wave detection unit that detects the photoacoustic waves generated from the photoacoustic wave generation portion and detects reflected acoustic waves reflected by transmission of acoustic waves to the subject; a Doppler signal generation unit that generates a Doppler signal on the basis of the reflected acoustic waves from a sample gate as a Doppler measurement target which have been detected by the acoustic wave detection unit; a reflected acoustic image generation unit that generates a reflected acoustic image on the basis of the reflected acoustic waves detected by the acoustic wave detection unit; an insert detection unit that detects a length direction of the insert on the basis of the reflected acoustic image; and a control unit that controls a steering direction of the sample gate on the basis of the length direction of the insert such that an angle θ formed between a straight line which extends in the length direction of the insert and a straight line which extends in the steering direction of the sample gate satisfies $0° \leq \theta < 90°$.

In the photoacoustic measurement device according to the invention, the control unit may set the steering direction of the sample gate, following a change in an insertion direction of the insert, in a state in which a magnitude of the angle θ is maintained.

In the photoacoustic measurement device according to the invention, the control unit may set the angle θ to 0°.

In the photoacoustic measurement device according to the invention, the control unit may store a plurality of steering angle candidates of the sample gate in advance and select a steering angle, at which the angle θ satisfies $0° \leq \theta < 90°$ and the steering direction of the sample gate is closest to the length direction of the insert, from the plurality of steering angle candidates.

The photoacoustic measurement device according to the invention may further comprise: a photoacoustic image generation unit that generates a photoacoustic image on the basis of the photoacoustic waves detected by the acoustic wave detection unit; and a tip position detection unit that detects a position of a tip of the insert on the basis of the photoacoustic image. The control unit may control a position of the sample gate such that the tip of the insert is included in the sample gate.

In the photoacoustic measurement device according to the invention, the control unit may control the position of the sample gate such that a center position of the sample gate is matched with the tip of the insert.

In the photoacoustic measurement device according to the invention, the control unit may set the position of the sample gate, following movement of the position of the tip of the insert, in a state in which a relative positional relationship between the position of the tip of the insert and the sample gate is maintained.

In the photoacoustic measurement device according to the invention, the insert detection unit may detect the length direction of the insert at each interval of two or more frames of the reflected acoustic images.

In the photoacoustic measurement device according to the invention, the insert detection unit may acquire an amount of change in an angle of the length direction of the insert. In a case in which the amount of change is equal to or less than a predetermined threshold value, the insert detection unit may increase the frame interval at which the length direction of the insert is detected.

The photoacoustic measurement device according to the invention may further comprise: a photoacoustic image generation unit that generates a photoacoustic image on the basis of the photoacoustic waves detected by the acoustic wave detection unit; and a tip position detection unit that detects a position of a tip of the insert on the basis of the photoacoustic image. In a case in which the position of the tip of the insert detected by the tip position detection unit is the same as a position of the tip of the insert in the photoacoustic image of a previous frame, the detection of the length direction of the insert based on the reflected acoustic image and the control of the steering direction of the sample gate based on the length direction of the insert may not be performed.

The photoacoustic measurement device according to the invention may further comprise a sound output unit that outputs sound information on the basis of the Doppler signal.

In the photoacoustic measurement device according to the invention, the insert may be a needle that is inserted into the subject.

According to the photoacoustic measurement device of the invention, in a case in which a photoacoustic image is generated on the basis of a detection signal of photoacoustic waves generated from the photoacoustic wave generation portion of the insert, a reflected acoustic image is generated on a detection signal of reflected acoustic waves generated by the transmission of acoustic waves. The length direction of the insert is detected on the basis of the reflected acoustic image. The steering direction of the sample gate which is a Doppler measurement target is controlled on the basis of the length direction of the insert such that the angle θ formed between the straight line extending in the length direction of the insert and the straight line extending in the steering direction of the sample gate satisfies $0° \leq \theta < 90°$. Therefore, it is possible to suppress the generation of an artifact in a Doppler signal caused by the reflected waves from the insert.

BRIEF DESCRIPTION OF THE DRAWINGS

FIG. 8 is a diagram illustrating a method for controlling the turn-on and turn-off of a process of detecting a length direction of a puncture needle on the basis of the amount of change in the angle of a length direction of the puncture needle.

DESCRIPTION OF THE PREFERRED EMBODIMENTS

Figure 1:
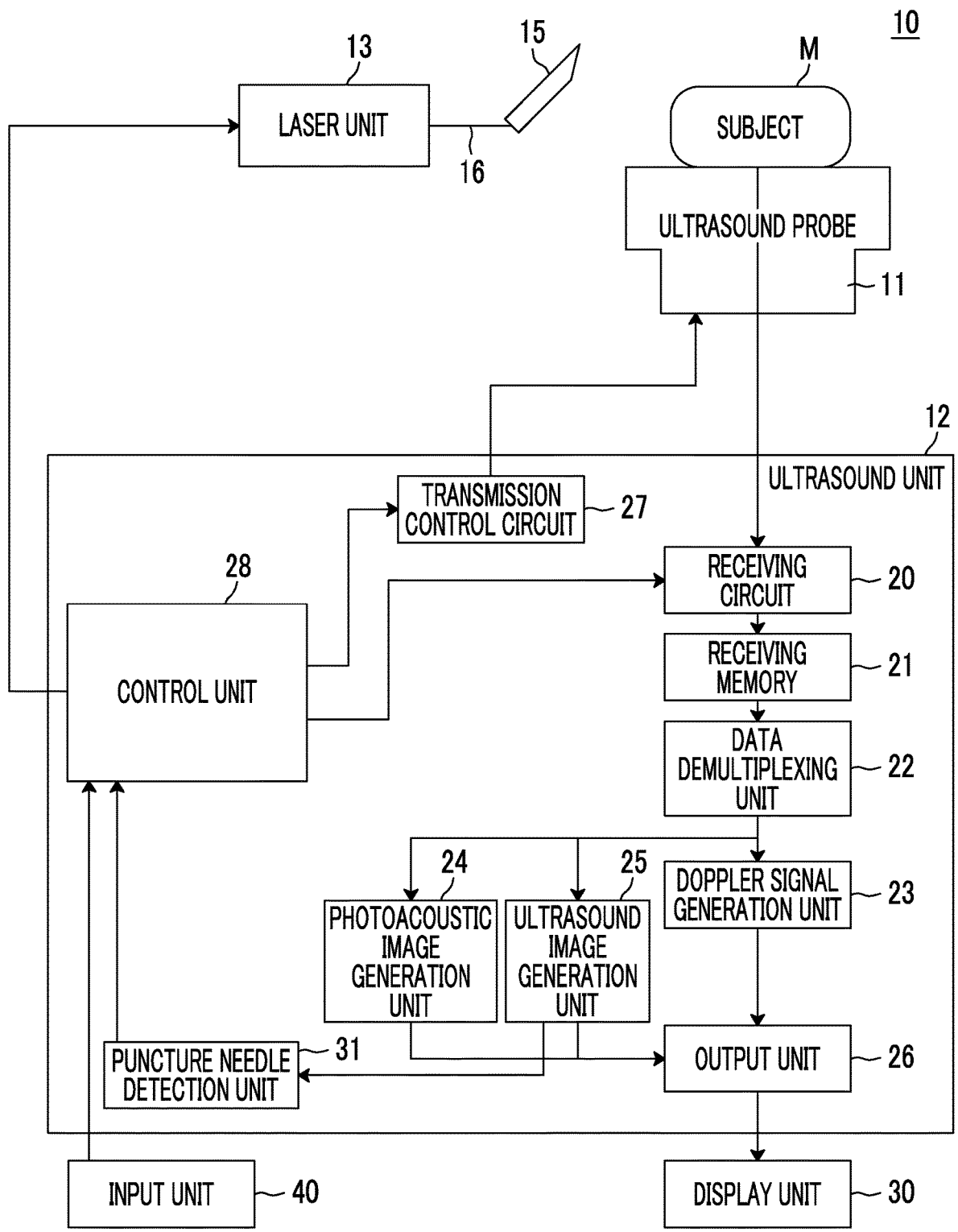
FIG. 1 is a block diagram schematically illustrating the configuration of a photoacoustic image generation apparatus using a first embodiment of a photoacoustic measurement device according to the invention.

Hereinafter, a photoacoustic image generation apparatus using a first embodiment of a photoacoustic measurement device according to the invention will be described in detail with reference to the drawings. FIG. 1 is a diagram schematically illustrating the configuration of a photoacoustic image generation apparatus 10 according to this embodiment.

As illustrated in FIG. 1, the photoacoustic image generation apparatus 10 according to this embodiment comprises an ultrasound probe 11, an ultrasound unit 12, a laser unit 13, and a puncture needle 15. The puncture needle 15 and the laser unit 13 are connected by an optical cable 16 having an optical fiber. The puncture needle 15 can be attached to and detached from the optical cable 16 and is disposable. In addition, in this embodiment, ultrasonic waves are used as acoustic waves. However, the invention is not limited to the ultrasonic waves. Acoustic waves with an audible frequency may be used as long as an appropriate frequency can be selected according to, for example, an inspection target or measurement conditions.

The laser unit 13 comprises a solid-state laser light source using, for example, yttrium aluminum garnet (YAG) and alexandrite. Laser light emitted from the solid-state laser light source of the laser unit 13 is guided by the optical cable 16 and is incident on the puncture needle 15. The laser unit 13 according to this embodiment emits pulsed laser light in a near-infrared wavelength range. The near-infrared wavelength range means a wavelength range from about 700 nm to 850 nm. In this embodiment, the solid-state laser light source is used. However, other laser light sources, such as a gas laser light source, may be used or light sources other than the laser light source may be used.

Figure 2:
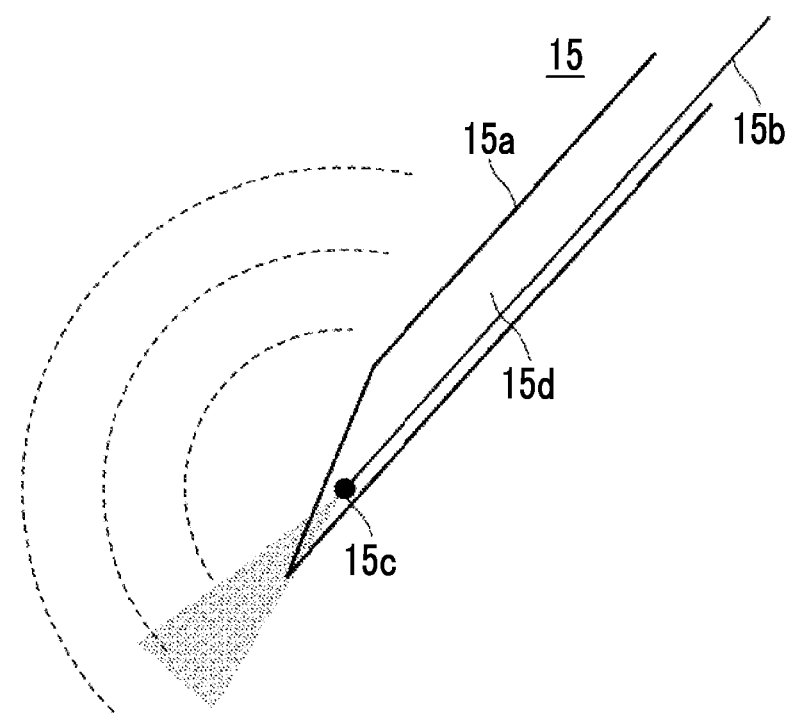
FIG. 2 is a cross-sectional view illustrating the configuration of a tip portion of a puncture needle.

The puncture needle 15 is an embodiment of an insert according to the invention and is a needle that is inserted into a subject M. FIG. 2 is a cross-sectional view including a center axis that extends in a length direction of the puncture needle 15. The puncture needle 15 includes a puncture needle main body 15a that has an opening at an acute tip and is formed in a hollow shape, an optical fiber 15b (corresponding to a light guide member according to the invention) that guides laser light emitted from the laser unit 13 to the vicinity of the opening of the puncture needle 15, and a photoacoustic wave generation portion 15c that absorbs laser light emitted from the optical fiber 15b and generates photoacoustic waves.

The optical fiber 15b and the photoacoustic wave generation portion 15c are provided in a hollow portion 15d of the puncture needle main body 15a. For example, the optical fiber 15b is connected to the optical fiber in the optical cable 16 (see FIG. 1) through an optical connector that is provided at the base end of the puncture needle 15. For example, a laser light of 0.2 mJ is emitted from a light emission end of the optical fiber 15b.

The photoacoustic wave generation portion 15c is provided at the light emission end of the optical fiber 15b and is provided in the vicinity of the tip of the puncture needle 15 and in the inner wall of the puncture needle main body 15a. The photoacoustic wave generation portion 15c absorbs the laser light emitted from the optical fiber 15b and generates photoacoustic waves. The photoacoustic wave generation portion 15c is made of, for example, an epoxy resin, a polyurethane resin, a fluorine resin, and silicone rubber with which a black pigment is mixed. In FIG. 2, the photoacoustic wave generation portion 15c is illustrated to be larger than the optical fiber 15b. However, the invention is not limited thereto. The photoacoustic wave generation portion 15c may have a size that is equal to the diameter of the optical fiber 15b.

The photoacoustic wave generation portion 15c is not limited to the above and a metal film or an oxide film having light absorptivity with respect to the wavelength of laser light may be used as the photoacoustic wave generation portion. An oxide film made of, for example, iron oxide, chromium oxide, or manganese oxide having high light absorptivity with respect to the wavelength of laser light can be used as the photoacoustic wave generation portion 15c. Alternatively, a metal film made of, for example, titanium (Ti) or platinum (Pt) that has a lower light absorptivity than an oxide and has a higher biocompatibility than an oxide may be used as the photoacoustic wave generation portion 15c. In addition, the position where the photoacoustic wave generation portion 15c is provided is not limited to the inner wall of the puncture needle main body 15a. For example, a metal film or an oxide film which is the photoacoustic wave generation portion 15c may be formed on the light emission end of the optical fiber 15b with a thickness of about 100 nm by vapor deposition such that the oxide film covers the light emission end. In this case, at least a portion of the laser light emitted from the light emission end of the optical fiber 15b is absorbed by the metal film or the oxide film covering the light emission end and photoacoustic waves are generated from the metal film or the oxide film.

The vicinity of the tip of the puncture needle 15 means a position where the photoacoustic wave generation portion 15c can generate photoacoustic waves capable of imaging the position of the tip of the puncture needle 15 with accuracy required for a needling operation in a case in which the tip of the optical fiber 15b and the photoacoustic wave generation portion 15c are disposed at the position. For example, the vicinity of the tip of the puncture needle 15 is the range of 0 mm to 3 mm from the tip to the base end of the puncture needle 15. In the subsequent embodiments, the meaning of the vicinity of the tip is the same as described above.

Returning to FIG. 1, the ultrasound probe 11 corresponds to an acoustic wave detection unit according to the invention and includes, for example, a plurality of ultrasound transducers which are one-dimensionally arranged. The ultrasound transducer is, for example, a piezoelectric element made of a polymer film, such as piezoelectric ceramics or polyvinylidene fluoride (PVDF).

The ultrasound probe 11 detects the photoacoustic waves generated from the photoacoustic wave generation portion 15c after the puncture needle 15 is inserted into a subject M. In addition, the ultrasound probe 11 performs the transmission of ultrasonic waves (acoustic waves) to the subject M and the detection of reflected ultrasonic waves (reflected acoustic waves) with respect to the transmitted ultrasonic waves, in addition to the detection of the photoacoustic waves.

In a case in which Doppler measurement is performed, the ultrasound probe 11 transmits pulsed ultrasonic waves and detects reflected ultrasonic waves with respect to the pulsed ultrasonic waves. In addition, in a case in which Doppler measurement is performed, the ultrasound probe 11 sets the position and steering direction of a sample gate, which is a Doppler measurement target, with respect to the subject M and transmits ultrasonic waves in the steering direction of the sample gate under the control of a control unit 28.

For example, a linear ultrasound probe, a convex ultrasound probe, or a sector ultrasound probe may be used as the ultrasound probe 11.

The ultrasound unit 12 includes a receiving circuit 20, a receiving memory 21, a data demultiplexing unit 22, a Doppler signal generation unit 23, a photoacoustic image generation unit 24, an ultrasound image generation unit 25, an output unit 26, a transmission control circuit 27, the control unit 28, and a puncture needle detection unit 31. The ultrasound unit 12 typically includes, for example, a processor, a memory, and a bus. A program related to, for example, a Doppler signal generation process, a photoacoustic image generation process, an ultrasound image generation process, and a process of detecting the length direction of the puncture needle 15 in an ultrasound image is incorporated into a memory in the ultrasound unit 12. The program is executed by the control unit 28 which is formed by a processor to implement the functions of the data demultiplexing unit 22, the Doppler signal generation unit 23, the photoacoustic image generation unit 24, the ultrasound image generation unit 25, the output unit 26, and the puncture needle detection unit 31. That is, each of these units is formed by the processor and the memory into which the program has been incorporated.

The hardware configuration of the ultrasound unit 12 is not particularly limited and can be implemented by an appropriate combination of, for example, a plurality of integrated circuits (ICs), a processor, an application specific integrated circuit (ASIC), a field-programmable gate array (FPGA), and a memory.

The receiving circuit 20 receives a detection signal output from the ultrasound probe 11 and stores the received detection signal in the receiving memory 21. The receiving circuit 20 typically includes a low-noise amplifier, a variable-gain amplifier, a low-pass filter, and an analog-to-digital converter (AD converter). The detection signal of the ultrasound probe 11 is amplified by the low-noise amplifier. Then, gain adjustment corresponding to a depth is performed by the variable-gain amplifier and a high-frequency component of the detection signal is cut by the low-pass filter. Then, the detection signal is converted into a digital signal by the AD convertor and the digital signal is stored in the receiving memory 21. The receiving circuit 20 is formed by, for example, one integral circuit (IC).

The ultrasound probe 11 outputs a detection signal of the photoacoustic waves and a detection signal of the reflected ultrasonic waves. The AD-converted detection signals (sampling data) of the photoacoustic waves and the reflected ultrasonic waves are stored in the receiving memory 21.

In a case in which a photoacoustic image is generated, the data demultiplexing unit 22 reads the detection signal of the photoacoustic waves from the receiving memory 21 and transmits the detection signal to the photoacoustic image generation unit 24. In addition, in a case in which an ultrasound image is generated, the data demultiplexing unit 22 reads the detection signal of the reflected ultrasonic waves from the receiving memory 21 and transmits the detection signal to the ultrasound image generation unit 25. Further, in a case in which Doppler measurement is performed, the data demultiplexing unit 22 reads a detection signal of reflected ultrasonic waves from the sample gate set by the control unit 28 and transmits the detection signal to the Doppler signal generation unit 23.

The Doppler signal generation unit 23 analyzes Doppler transition in the sample gate on the basis of the detection signal of the reflected ultrasonic waves generated by the transmission of the pulsed ultrasonic waves to generate a Doppler signal indicating a blood flow rate.

The photoacoustic image generation unit 24 generates a photoacoustic image on the basis of the detection signal of the photoacoustic waves detected by the ultrasound probe 11. The photoacoustic image generation process includes, for example, image reconfiguration, such as phasing addition, detection, and logarithmic conversion.

The ultrasound image generation unit 25 (corresponding to a reflected acoustic image generation unit according to the invention) generates an ultrasound image (reflected acoustic image) on the basis of the detection signal of the reflected ultrasonic waves detected by the ultrasound probe 11. The ultrasound image generation process includes image reconfiguration, such as phasing addition, detection, and logarithmic conversion.

The output unit 26 displays the photoacoustic image and the ultrasound image on a display unit 30 such as a display device. In addition, the output unit 26 displays a waveform indicating the blood flow rate on the display unit 30 on the basis of the Doppler signal indicating the blood flow rate.

The puncture needle detection unit 31 corresponds to an insert detection unit according to the invention, detects an image of the puncture needle 15 from the ultrasound image generated by the ultrasound image generation unit 25 on the basis of the ultrasound image, and detects the length direction of the puncture needle 15 on the basis of the image. As a method for detecting the image of the puncture needle 15, for example, a binarization process is performed for the ultrasound image and a region in which white pixels are continuously distributed may be detected as an image region of the puncture needle 15. In addition, the invention is not limited thereto and the image of the puncture needle 15 may be detected by other known types of image processing.

The control unit 28 controls each component in the ultrasound unit 12. For example, in a case in which a photoacoustic image is acquired, the control unit 28 transmits a trigger signal to the laser unit 13 such that the laser unit 13 emits pulsed laser light. In addition, the control unit 28 transmits a sampling trigger signal to the receiving circuit 20 to control, for example, the sampling start time of the photoacoustic waves with the emission of the laser light. The detection signal of the photoacoustic waves which has been received by the receiving circuit 20 and then converted into a digital signal is stored in the receiving memory 21.

In a case in which an ultrasound image is acquired, the control unit 28 transmits an ultrasound transmission trigger signal for commanding the transmission of ultrasonic waves to the transmission control circuit 27. In a case in which the ultrasound transmission trigger signal is received, the transmission control circuit 27 directs the ultrasound probe 11 to transmit ultrasonic waves. The control unit 28 transmits the sampling trigger signal to the receiving circuit 20 according to the transmission time of ultrasonic waves such that the receiving circuit 20 starts the sampling of the reflected ultrasonic waves. The detection signal of the ultrasonic waves which has been received by the receiving circuit 20 and then converted into a digital signal is stored in the receiving memory 21.

In a case in which Doppler measurement is performed, the control unit 28 transmits a pulsed ultrasound transmission trigger signal for commanding the transmission of pulsed ultrasonic waves to the transmission control circuit 27. In a case in which the pulsed ultrasound transmission trigger signal is received, the transmission control circuit 27 directs the ultrasound probe 11 to transmit pulsed ultrasonic waves. The control unit 28 transmits the sampling trigger signal to the receiving circuit 20 according to the transmission time of pulsed ultrasonic waves such that the receiving circuit 20 starts the sampling of the reflected ultrasonic waves. The detection signal of the ultrasonic waves which has been received by the receiving circuit 20 and then converted into a digital signal is stored in the receiving memory 21.

In addition, in a case in which Doppler measurement is performed, the control unit 28 sets a sample gate which is a Doppler measurement target as described above. Then, the control unit 28 sets the steering direction of the sample gate and controls the ultrasound probe 11 such that ultrasonic waves are transmitted in the steering direction of the sample gate. Then, the Doppler signal generation unit 23 generates a Doppler signal on the basis of the positional information of the sample gate set by the control unit 28.

Here, in a case in which needling is performed with the puncture needle 15 having the photoacoustic wave generation portion 15c as described above and Doppler measurement is performed by a pulsed Doppler method, if the insertion direction (length direction) of the puncture needle 15 and the steering direction of the sample gate are not appropriately set, a signal caused by reflected waves from the puncture needle 15 is included as an artifact in the detection signal of the reflected ultrasonic waves in the Doppler measurement, which makes it difficult to acquire an accurate Doppler signal.

Figure 3:
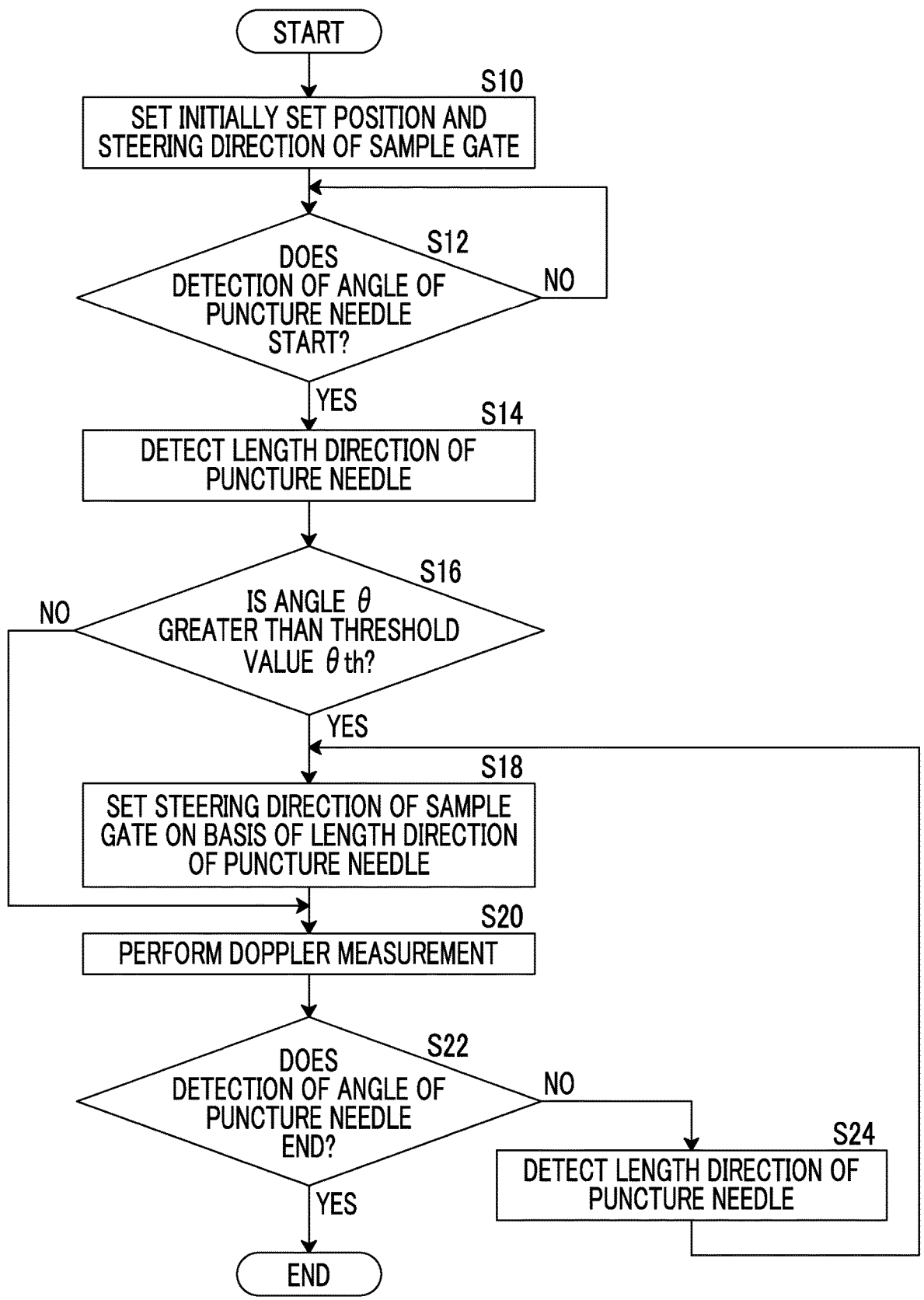
FIG. 3 is a flowchart illustrating a method for setting a steering direction of a sample gate in the photoacoustic image generation apparatus according to the first embodiment.

For this reason, the control unit 28 according to this embodiment sets the steering direction of the sample gate to an appropriate direction in order to suppress the generation of the artifact. Hereinafter, a method for setting the steering direction of the sample gate in the control unit 28 will be described with reference to a flowchart illustrated in FIG. 3 and FIG. 4.

First, the control unit 28 sets the initially set position and steering direction of the sample gate (S10). The initially set position and steering direction of the sample gate may be stored in advance or the information of the initially set position and steering direction of the sample gate may be set and input by the user, such as a doctor, through an input unit 40 (see FIG. 1). In addition, an ultrasound image may be displayed on the display unit 30 (see FIG. 1) such that the user sets and inputs the initially set position and steering direction of the sample gate in the ultrasound image with the input unit 40. In addition, the initially set position of the sample gate is set to a position where a blood vessel is assumed to be present in the subject M and the steering direction of the sample gate is set to a direction assumed to be parallel to, for example, a direction in which the blood vessel extends.

Then, the control unit 28 checks whether the user has input a command to start the detection of the angle of the puncture needle 15. In a case in which the angle detection start command has been input (S12, YES), the control unit 28 starts a process of detecting the length direction of the puncture needle 15 (S14). In addition, the user inputs the angle detection start command and an angle detection end command with the input unit 40 (see FIG. 1).

Specifically, ultrasonic waves are transmitted from the ultrasound probe 11 to the subject M and a detection signal of reflected ultrasonic waves detected by the ultrasound probe 11 is received by the receiving circuit 20 and is stored in the receiving memory 21 under the control of the control unit 28. Then, the data demultiplexing unit 22 transmits the detection signal of the reflected ultrasonic waves from the receiving memory 21 to the ultrasound image generation unit 25 and the ultrasound image generation unit 25 generates an ultrasound image of one frame.

The ultrasound image of one frame generated by the ultrasound image generation unit 25 is input to the puncture needle detection unit 31 and the puncture needle detection unit 31 detects the length direction of the puncture needle 15 (S14).

Figure 4:
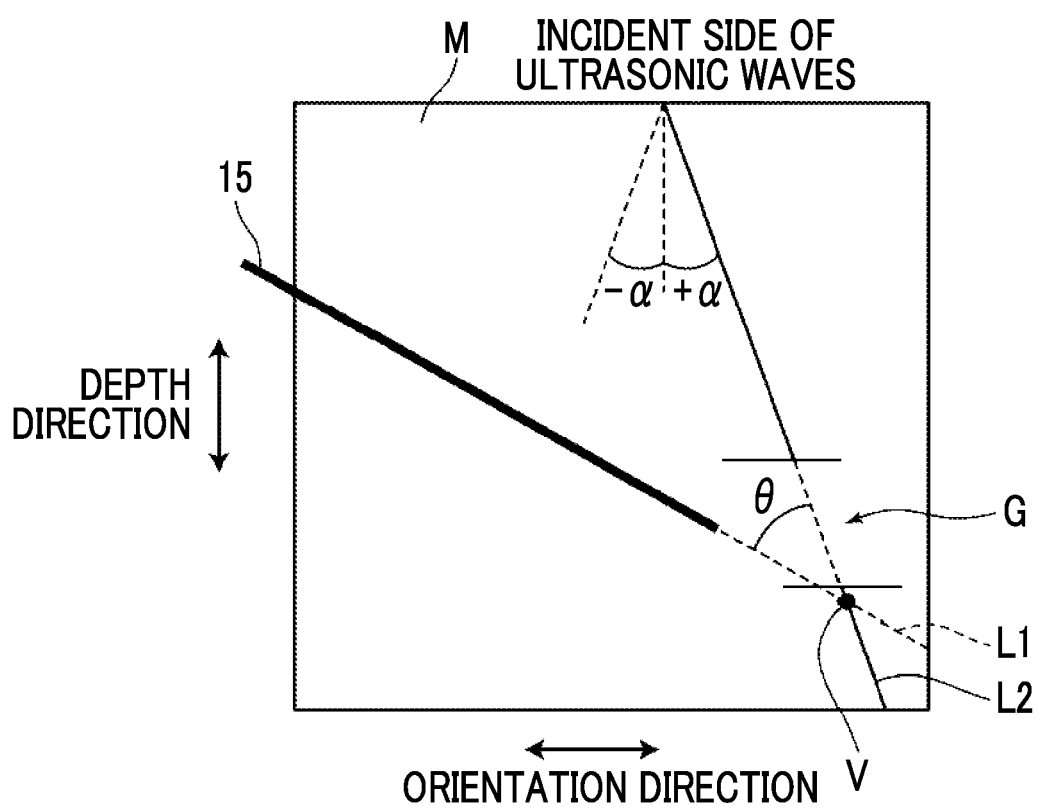
FIG. 4 is a diagram illustrating the method for setting the steering direction of the sample gate in the photoacoustic image generation apparatus according to the first embodiment.

Then, the information of the length direction of the puncture needle 15 detected by the puncture needle detection unit 31 is input to the control unit 28. As illustrated in FIG. 4, the control unit 28 calculates an angle θ formed between a straight line L1 which extends in the length direction of the puncture needle 15 and a straight line L2 which extends in the initially set steering direction of the sample gate on the basis of the input information of the length direction of the puncture needle 15 and checks whether the angle θ is greater than a predetermined threshold value θth.

Here, in the invention, the angle formed between the straight line which extends in the length direction of the insert and the straight line which extends in the steering direction of the sample gate means an angle formed between a straight line which extends in the length direction of the puncture needle 15 from an insertion starting point of the puncture needle 15 and a straight line which extends in the steering direction from the incident side of ultrasonic waves in a case in which an intersection point of the straight line L1 extending in the length direction of the insert (puncture needle 15) and the straight line L2 extending in the steering direction of a sample gate G is a vertex V as illustrated in FIG. 4.

In addition, a value satisfying 0°≤θth<90° is set as the threshold value θth. Most preferably, θth is 0°. However, a value satisfying 0°<θth≤10°, a value satisfying 0°<θth≤15°, a value satisfying 0°<θth≤30°, or a value satisfying 0°<θth≤45° may be set. In a case in which the threshold value θth is 0°, checking whether the angle θ is greater than the threshold value θth is synonymous with checking whether the straight line L1 and the straight line L2 are parallel to each other.

Then, in a case in which the angle θ is equal to or less than the threshold value θth (S16, NO), the control unit 28 determines that the insertion direction (length direction) of the puncture needle 15 and the steering direction of the sample gate are appropriate and performs Doppler measurement while maintaining the initially set position and steering direction of the sample gate G (S20).

Specifically, the ultrasound probe 11 transmits pulsed ultrasonic waves. Then, the ultrasound probe 11 detects reflected ultrasonic waves generated by the transmission of the pulsed waves. Then, a detection signal of the reflected ultrasonic waves is received by the receiving circuit 20 and is stored in the receiving memory 21. Then, the data demultiplexing unit 22 transmits the detection signal of the reflected ultrasonic waves from the receiving memory 21 to the Doppler signal generation unit 23. The Doppler signal generation unit 23 generates a Doppler signal on the basis of the initially set information of the sample gate. Then, a waveform signal based on the Doppler signal is output from the output unit 26 to the display unit 30 and is displayed.

On the other hand, in a case in which the angle θ is greater than the threshold value θth in S16 (S16, YES), the control unit 28 sets the steering direction of the sample gate on the basis of the length direction of the puncture needle 15 detected by the puncture needle detection unit 31 (S18). Specifically, the control unit 28 sets the steering direction of the sample gate G such that the angle θ formed between the straight line L1 extending in the length direction of the puncture needle 15 and the straight line L2 extending in the steering direction of the sample gate G is the threshold value θth as illustrated in FIG. 4. Then, after the steering direction of the sample gate G is set, the control unit 28 performs Doppler measurement in the same way as described above (S20). In addition, in this embodiment, it is assumed that the position of the sample gate G is the initial set position of the sample gate G.

Then, the control unit 28 checks whether the user has input a command to end the detection of the angle of the puncture needle 15 (S22). In a case in which the angle detection end command has not been input (S22, NO), the control unit 28 detects the length direction of the puncture needle 15 on the basis of an ultrasound image of the next frame (S24). Then, the control unit 28 sets the steering direction of the sample gate on the basis of the length direction of the puncture needle 15 in the ultrasound image of the next frame (S18). Specifically, similarly to the above, the control unit 28 sets the steering direction of the sample gate G such that the angle θ formed between the straight line L1 extending in the length direction of the puncture needle 15 and the straight line L2 extending in the steering direction of the sample gate G is the threshold value θth. Then, after the steering direction of the sample gate G is set, the control unit 28 performs Doppler measurement in the same way as described above (S20).

Then, in S22, the control unit 28 repeatedly performs the detection of the length direction of the puncture needle 15 in S24, the setting of the steering direction of the sample gate in S18, and the Doppler measurement in S20 until the user inputs a command to end the detection of the angle of the puncture needle 15. The control unit 28 performs this process to set the steering direction of the sample gate following a change in the insertion direction of the puncture needle 15, in a state in which the angle θ formed between the straight line L1 extending in the length direction of the puncture needle 15 and the straight line L2 extending in the steering direction of the sample gate G is maintained at the threshold value θth.

Then, in a case in which the angle detection end command is input in S22 (S22, YES), the control unit 28 ends the process.

The photoacoustic image generation apparatus 10 according to the first embodiment generates an ultrasound image on the basis of the detection signal of the reflected ultrasonic waves generated by the transmission of ultrasonic waves, detects the length direction of the puncture needle 15 on the basis of the ultrasound image, and controls the steering direction of the sample gate which is a Doppler measurement target on the basis of the length direction of the puncture needle 15 such that the angle θ formed between the straight line extending in the length direction of the puncture needle 15 and the straight line extending in the steering direction of the sample gate satisfies 0°≤θ<90°. Therefore, it is possible to suppress the generation of an artifact of a Doppler signal caused by the reflected waves from the puncture needle 15.

In the photoacoustic image generation apparatus 10 according to the first embodiment, in a case in which the angle θ is greater than the threshold value θth, the steering direction of the sample gate is set such that the angle θ is the threshold value θth. However, the invention is not limited thereto. For example, the control unit 28 may store a plurality of steering angle candidates of the sample gate, select a steering angle candidate at which the angle θ satisfies 0°≤θ<90° and the steering direction of the sample gate is closest to the length direction of the puncture needle 15 from the plurality of steering angle candidates, and set the steering direction of the sample gate to the direction indicated by the selected steering angle. In addition, the steering angle of the sample gate is an angle indicating the inclination of the steering direction of the sample gate with respect to the depth direction of the subject M and is, for example, an angle of +α or −α illustrated in FIG. 4. As the steering angle candidates, for example, ±10°, ±20°, and ±30° are stored in the control unit 28 in advance. As described above, the control unit 28 sets one steering angle from the steering angle candidates and sets the steering direction of the sample gate to the direction indicated by the steering angle.

Next, a photoacoustic image generation apparatus 10 using a second embodiment of the photoacoustic measurement device according to the invention will be described. In the photoacoustic image generation apparatus 10 according to the first embodiment, in a case in which the steering direction of the sample gate is set on the basis of the length direction of the puncture needle 15, the position of the sample gate is the initially set position of the sample gate. However, the photoacoustic image generation apparatus 10 according to the second embodiment controls the position of the sample gate.

Figure 5:
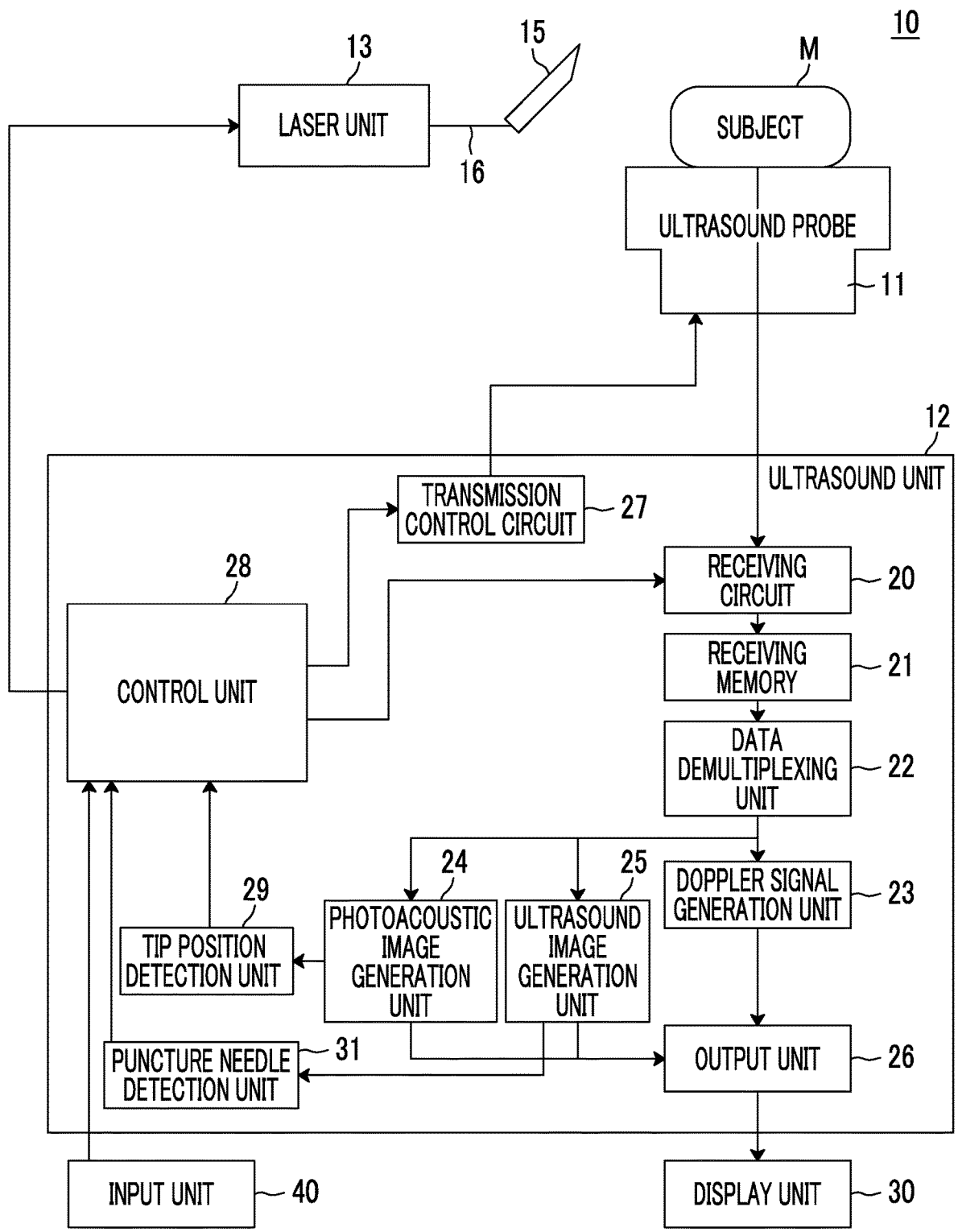
FIG. 5 is a block diagram schematically illustrating the configuration of a photoacoustic image generation apparatus using a second embodiment of the photoacoustic measurement device according to the invention.

FIG. 5 is a block diagram illustrating the configuration of the photoacoustic image generation apparatus 10 according to the second embodiment. As illustrated in FIG. 5, the photoacoustic image generation apparatus 10 according to the second embodiment differs from the photoacoustic image generation apparatus 10 according to the first embodiment in that it further comprises a tip position detection unit 29. The other configurations are the same as those in the photoacoustic image generation apparatus 10 according to the first embodiment.

The tip position detection unit 29 detects the position of the tip of the puncture needle 15 on the basis of the photoacoustic image generated by the photoacoustic image generation unit 24. As a method for detecting the position of the tip of the puncture needle 15, for example, a method may be used which detects the position of a maximum brightness point in the photoacoustic image as the position of the tip of the puncture needle 15.

In a case in which the position of the tip of the puncture needle 15 is detected on the basis of the photoacoustic image as described above, in practice, an artifact of light or an artifact of sound is generated and a photoacoustic image in which photoacoustic waves are detected from a plurality of positions is likely to be generated and the original position of the tip of the puncture needle 15 is unlikely to be specified.

For this reason, the photoacoustic image generated by the photoacoustic image generation unit 24 is not used as it is, but, for example, a smoothing process may be performed for the photoacoustic image to prevent erroneous detection caused by the artifact. Specifically, the smoothing process is performed for the photoacoustic image subjected to detection and logarithmic conversion. For example, a filtering process using a Gaussian filter can be used as the smoothing process.

Then, a binarization process is performed for the photoacoustic image subjected to the smoothing process to generate a binary image. Then, a region in which white pixels are continuously distributed is detected from the binary image to detect the position of the tip of the puncture needle 15. In this way, it is possible to detect the position of the tip of the puncture needle 15 with higher accuracy.

Figure 6:
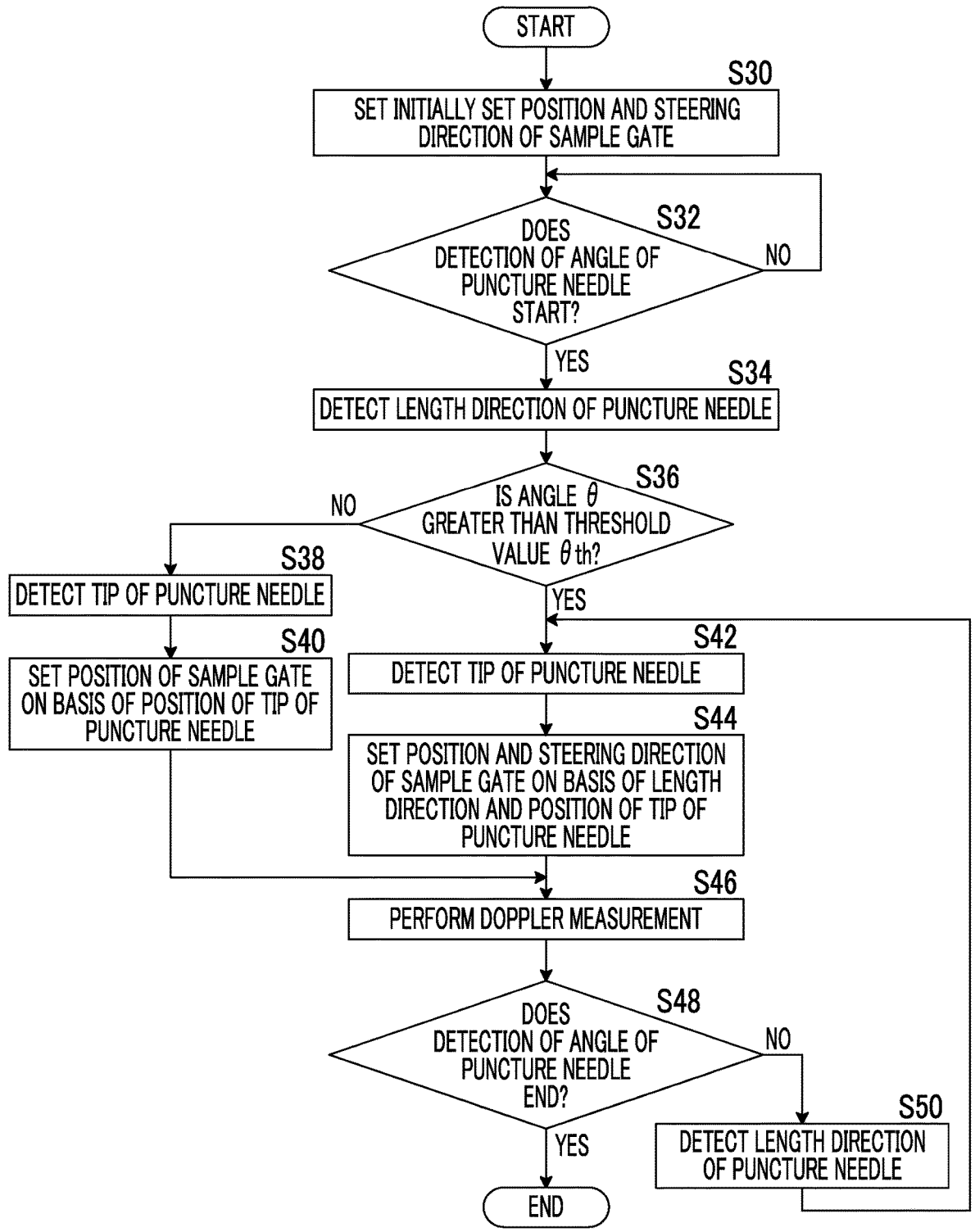
FIG. 6 is a flowchart illustrating a method for setting the position and steering direction of a sample gate in the photoacoustic image generation apparatus according to the second embodiment.

Next, a method for setting the position of a sample gate in the photoacoustic image generation apparatus 10 according to the second embodiment will be described with reference to a flowchart illustrated in FIG. 6 and FIG. 7.

In the photoacoustic image generation apparatus 10 according to the second embodiment, first, the control unit 28 sets the initially set position and steering direction of the sample gate (S30). A method for setting the initially set position and steering direction of the sample gate is the same as that in the first embodiment.

Then, the control unit 28 checks whether the user has input a command to start the detection of the angle of the puncture needle 15. In a case in which the angle detection start command has been input (S32, YES), the control unit 28 starts a process of detecting the length direction of the puncture needle 15 (S34).

Specifically, similarly to the first embodiment, ultrasonic waves are transmitted from the ultrasound probe 11 to the subject M and a detection signal of reflected ultrasonic waves detected by the ultrasound probe 11 is received by the receiving circuit 20 and is stored in the receiving memory 21 under the control of the control unit 28. Then, the data demultiplexing unit 22 transmits the detection signal of the reflected ultrasonic waves from the receiving memory 21 to the ultrasound image generation unit 25 and the ultrasound image generation unit 25 generates an ultrasound image of one frame.

Then, the ultrasound image of one frame generated by the ultrasound image generation unit 25 is input to the puncture needle detection unit 31 and the puncture needle detection unit 31 detects the length direction of the puncture needle 15 (S34).

Then, the information of the length direction of the puncture needle 15 detected by the puncture needle detection unit 31 is input to the control unit 28. As illustrated in FIG. 7, the control unit 28 calculates an angle $\theta$ formed between a straight line L1 which extends in the length direction of the puncture needle 15 and a straight line L2 which extends in the initially set steering direction of the sample gate on the basis of the input information of the length direction of the puncture needle 15 and checks whether the angle $\theta$ is greater than a predetermined threshold value $\theta$th.

Then, in a case in which the angle $\theta$ is equal to or less than the threshold value $\theta$th (S36, NO), the control unit 28 determines that the insertion direction (length direction) of the puncture needle 15 and the steering direction of the sample gate are appropriate and does not change the initially set steering direction of the sample gate G.

Then, a process of detecting the tip of the puncture needle 15 is performed (S38). Specifically, a detection signal of the photoacoustic waves generated from the photoacoustic wave generation portion 15c of the puncture needle 15 is received by the receiving circuit 20 and is stored in the receiving memory 21 under the control of the control unit 28. Then, the data demultiplexing unit 22 transmits the detection signal of the photoacoustic waves from the receiving memory 21 to the photoacoustic image generation unit 24 and the photoacoustic image generation unit 24 generates a photoacoustic image of one frame.

The photoacoustic image of one frame generated by the photoacoustic image generation unit 24 is input to the tip position detection unit 29. The tip position detection unit 29 detects the position of a tip portion of the puncture needle 15.

Figure 7:
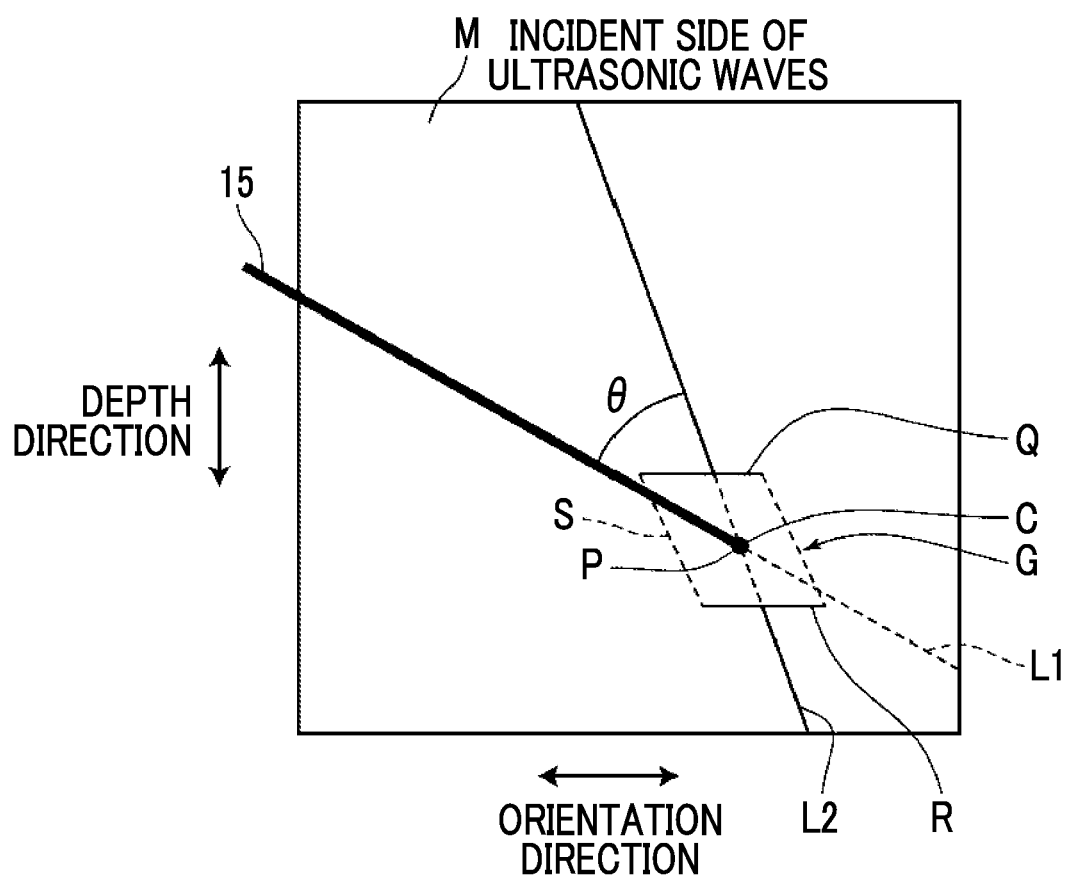
FIG. 7 is a diagram illustrating the method for setting the position and steering direction of the sample gate in the photoacoustic image generation apparatus according to the second embodiment.

Then, as illustrated in FIG. 7, the control unit 28 sets the position of the sample gate G such that a tip P of the puncture needle 15 is included in a rectangular region S defined by an upper end Q and a lower end R of the sample gate G (S40). In this embodiment, the position of the sample gate G is set such that a center position C of the rectangular region S is matched with the tip P of the puncture needle 15. However, the invention is not limited thereto. A position other than the center position C may be matched with the tip P of the puncture needle 15. In addition, it is preferable that the width of the rectangular region S in an orientation direction is a width corresponding to one line. One line is a region of the subject from which a detection signal is acquired by phasing addition centering on one ultrasound transducer (piezoelectric element). The width of the rectangular region S is not limited to a width corresponding to one line and may be a width corresponding to 2 or 3 lines.

Then, after the position of the sample gate G is set as described above, Doppler measurement is performed in the same way as described above (S46).

On the other hand, in a case in which the angle $\theta$ is greater than the threshold value $\theta$th in S36, (S36, YES), a process of detecting the tip of the puncture needle 15 is performed in the same way as described above (S42).

Then, the control unit 28 sets the steering direction and position of the sample gate on the basis of the position of the tip of the puncture needle 15 and the length direction of the puncture needle 15 detected by the puncture needle detection unit 31 (S44). Specifically, similarly to the first embodiment, the control unit 28 sets the steering direction of the sample gate G such that the angle $\theta$ formed between the straight line L1 extending in the length direction of the puncture needle 15 and the straight line L2 extending in the steering direction of the sample gate G is the threshold value $\theta$th as illustrated in FIG. 7. In addition, the control unit 28 sets the position of the sample gate G such that the tip P of the puncture needle 15 is included in the rectangular region S defined by the upper end Q and the lower end R of the sample gate G as illustrated in FIG. 7.

Then, after the position and steering direction of the sample gate G are set, Doppler measurement is performed in the same way as described above (S46).

Then, the control unit 28 checks whether the user has input a command to end the detection of the angle of the puncture needle 15 (S48). In a case in which the angle detection end command has not been input (S48, NO), the control unit 28 detects the length direction of the puncture needle 15 on the basis of an ultrasound image of the next frame (S50). Then, the control unit 28 detects the position of the tip of the puncture needle 15 on the basis of a photoacoustic image of the next frame (S42).

Then, the control unit 28 sets the steering direction of the sample gate on the basis of the length direction of the puncture needle 15 in the ultrasound image of the next frame and sets the position of the sample gate on the basis of the position of the tip of the puncture needle 15 in the photoacoustic image of the next frame (S44). Then, after the position and steering direction of the sample gate G are set, Doppler measurement is performed in the same way as described above (S46).

Then, in S48, the control unit 28 repeatedly performs the detection of the length direction of the puncture needle 15 in S50, the detection of the position of the tip of the puncture needle 15 in S42, the setting of the position and steering direction of the sample gate in S44, and the Doppler measurement in S46 until the user inputs a command to end the detection of the angle of the puncture needle 15. The control unit 28 performs this process to set the steering direction of the sample gate following a change in the insertion direction of the puncture needle 15, in a state in which the angle $\theta$ formed between the straight line L1 extending in the length direction of the puncture needle 15 and the straight line L2 extending in the steering direction of the sample gate G is maintained at the threshold value $\theta$th. In addition, the control unit 28 can set the position of the sample gate following the movement of the position of the tip of the puncture needle 15, in a state in which the relative positional relationship between the position of the tip of the puncture needle 15 and the sample gate is maintained. Therefore, it is possible to always set the sample gate, which is a Doppler measurement target, in the vicinity of the tip of the puncture needle 15 and thus to immediately check a blood flow rate in the vicinity of the tip of the puncture needle 15.

Then, in a case in which the angle detection end command is input in S48 (S48, YES), the control unit 28 ends the process.

In the photoacoustic image generation apparatus 10 according to the second embodiment, for each frame for acquiring an ultrasound image, the length direction of the puncture needle 15 is detected on the basis of the ultrasound image. However, since the length direction of the puncture needle 15 is not frequently changed, it is not necessary to detect the length direction of the puncture needle 15 for each frame. Therefore, the length direction of the puncture needle 15 may be detected at each interval of two or more frames. In this case, it is possible to reduce the load of the detection process of the puncture needle 15.

In addition, the puncture needle detection unit 31 may acquire the amount of change in the angle of the length direction of the puncture needle 15 on the basis of the length direction of the puncture needle 15 and the frame interval at which the process of detecting the length direction of the puncture needle 15 is performed may be increased in a case in which the amount of change is equal to or less than a predetermined threshold value. In a case in which there is no change in the angle of the length direction of the puncture needle 15, the process of detecting the length direction of the puncture needle 15 may not be performed (may be omitted) for a reflected acoustic image of the next frame. FIG. 8 is a diagram illustrating an example of a case in which the timing of the process of detecting the length direction of the puncture needle 15 is controlled as described above. Here, the angle of the length direction of the puncture needle 15 means an acute angle among the angles formed between a straight line extending in the length direction of the puncture needle 15 and a straight line extending in the depth direction.

As illustrated in FIG. 8, in a second frame, there is no change in the angle of the length direction of the puncture needle 15 from a first frame. Therefore, in a third frame, the process of detecting the length direction of the puncture needle 15 is not performed. In a fourth frame, the process of detecting the length direction of the puncture needle 15 is performed again. However, since the angle has not been changed from the previously detected angle, the process of detecting the length direction of the puncture needle 15 is not performed in the fifth and sixth frames. That is, the frame interval at which the process of detecting the length direction of the puncture needle 15 is not performed is increased. Then, in a seventh frame, the process of detecting the length direction of the puncture needle 15 is performed again. However, since the angle has not been changed from the previously detected angle, the frame interval at which the process of detecting the length direction of the puncture needle 15 is not performed is further increased. That is, the process of detecting the length direction of the puncture needle 15 is not performed in three frames, that is, eighth to tenth frames.

Then, in an eleventh frame, the process of detecting the length direction of the puncture needle 15 is performed again. In the process of detecting the length direction of the puncture needle 15 for the eleventh frame, the angle has been changed from the previously detected angle. Therefore, in a twelfth frame, the process of detecting the length direction of the puncture needle 15 is also performed. In the process of detecting the length direction of the puncture needle 15 for the twelfth frame, the angle has been changed from the previously detected angle. Therefore, in a thirteenth frame, the process of detecting the length direction of the puncture needle 15 is also performed. In the process of detecting the length direction of the puncture needle 15 for the thirteenth frame, the angle has been changed from the previously detected angle. Therefore, in a fourteenth frame, the process of detecting the length direction of the puncture needle 15 is also performed. Since the angle has not been changed from the previously detected angle in the fourteenth frame, the process of detecting the length direction of the puncture needle 15 is not performed in a fifteenth frame. Then, in a sixteenth frame, the process of detecting the length direction of the puncture needle 15 is performed again. However, since the angle has not been changed from the previously detected angle, the process of detecting the length direction of the puncture needle 15 is not performed in seventeenth and eighteenth frames. Then, in a nineteenth frame, the process of detecting the length direction of the puncture needle 15 is performed again. However, since the angle has not been changed from the previously detected angle, the process of detecting the length direction of the puncture needle 15 is not performed in a twentieth frame.

Figure 9:
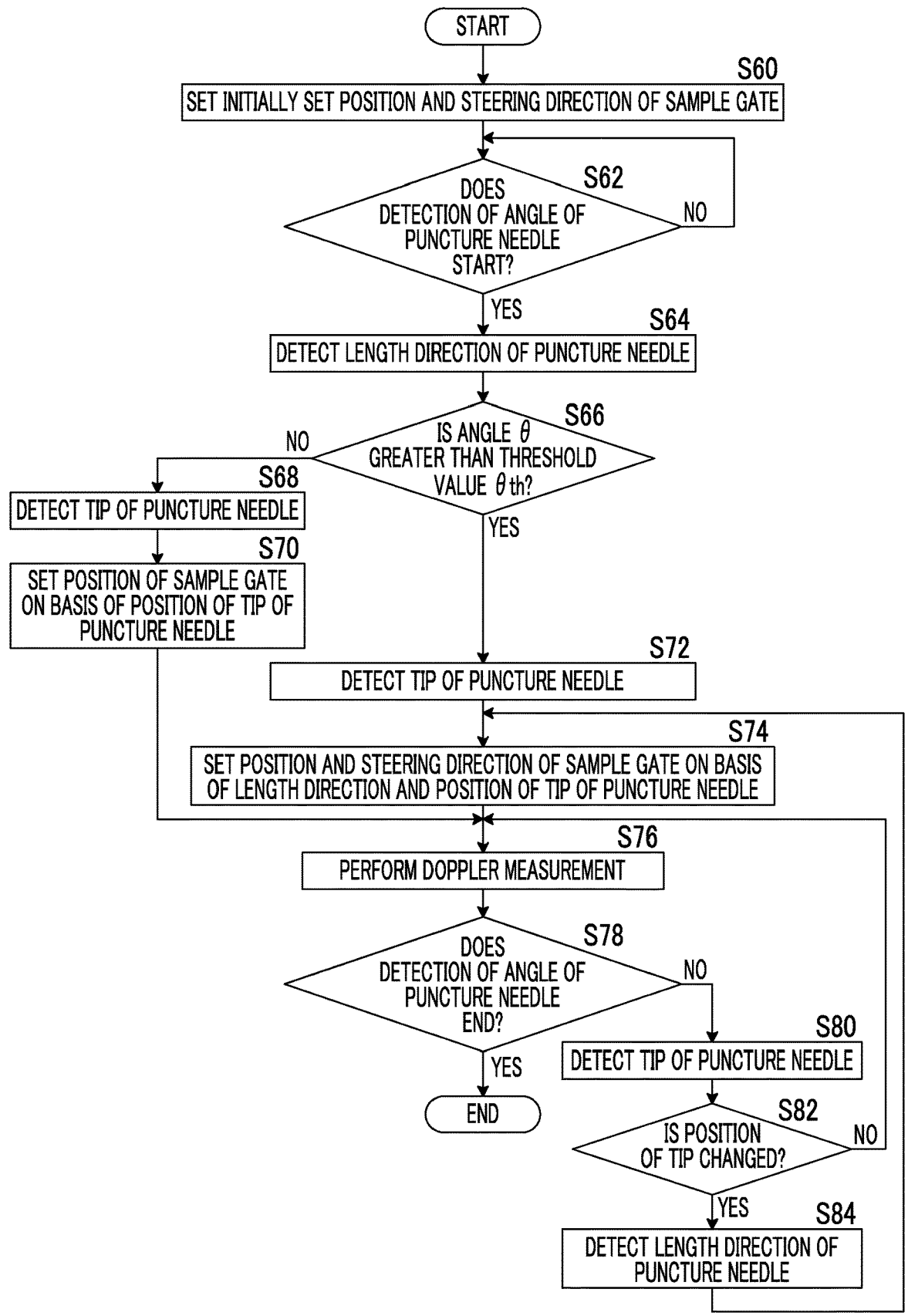
FIG. 9 is a flowchart illustrating a method for controlling the turn-on and turn-off of the process of detecting the length direction of the puncture needle on the basis of a change in the position of a tip portion of the puncture needle.

In the photoacoustic image generation apparatus 10 according to the second embodiment, in the process of detecting the position of the tip of the puncture needle 15, in a case in which the position of the tip of the puncture needle 15 has not been changed from the position of the tip in the photoacoustic image of the previous frame, the process of detecting the length direction of the puncture needle 15 and the process of setting the position and steering direction of the sample gate on the basis of the position of the tip of the puncture needle 15 and the length direction of the puncture needle 15 may not be performed (may be omitted). FIG. 9 is a flowchart in this case.

In the flowchart illustrated in FIG. 9, a process in S60 and S62 and S64 to S76 based on an ultrasound image and a photoacoustic image of the initial frame is the same as that in the second embodiment.

Then, the tip of the puncture needle 15 is detected on the basis of the photoacoustic images of the second and subsequent frames (S80). At that time, in a case in which the position of the tip has not been changed from the position of the tip in the photoacoustic image of the previous frame (S82, NO), the process of detecting the length direction of the puncture needle 15 in S84 and the process of setting the position and steering direction of the sample gate in S74 are not performed and Doppler measurement is performed (S76). On the other hand, in a case in which the position of the tip has been changed from the position of the tip in the photoacoustic image of the previous frame in S82 (S82, YES), the process of detecting the length direction of the puncture needle 15 in S84 and the process of setting the position and steering direction of the sample gate in S74 are performed and then Doppler measurement is performed (S76).

Then, in S78, the process in S80 to S84 and S74 to S76 is repeatedly performed until the user inputs a command to end the detection of the angle of the puncture needle 15. In a case in which the angle detection end command is input in S78, the process ends.

Figure 10:
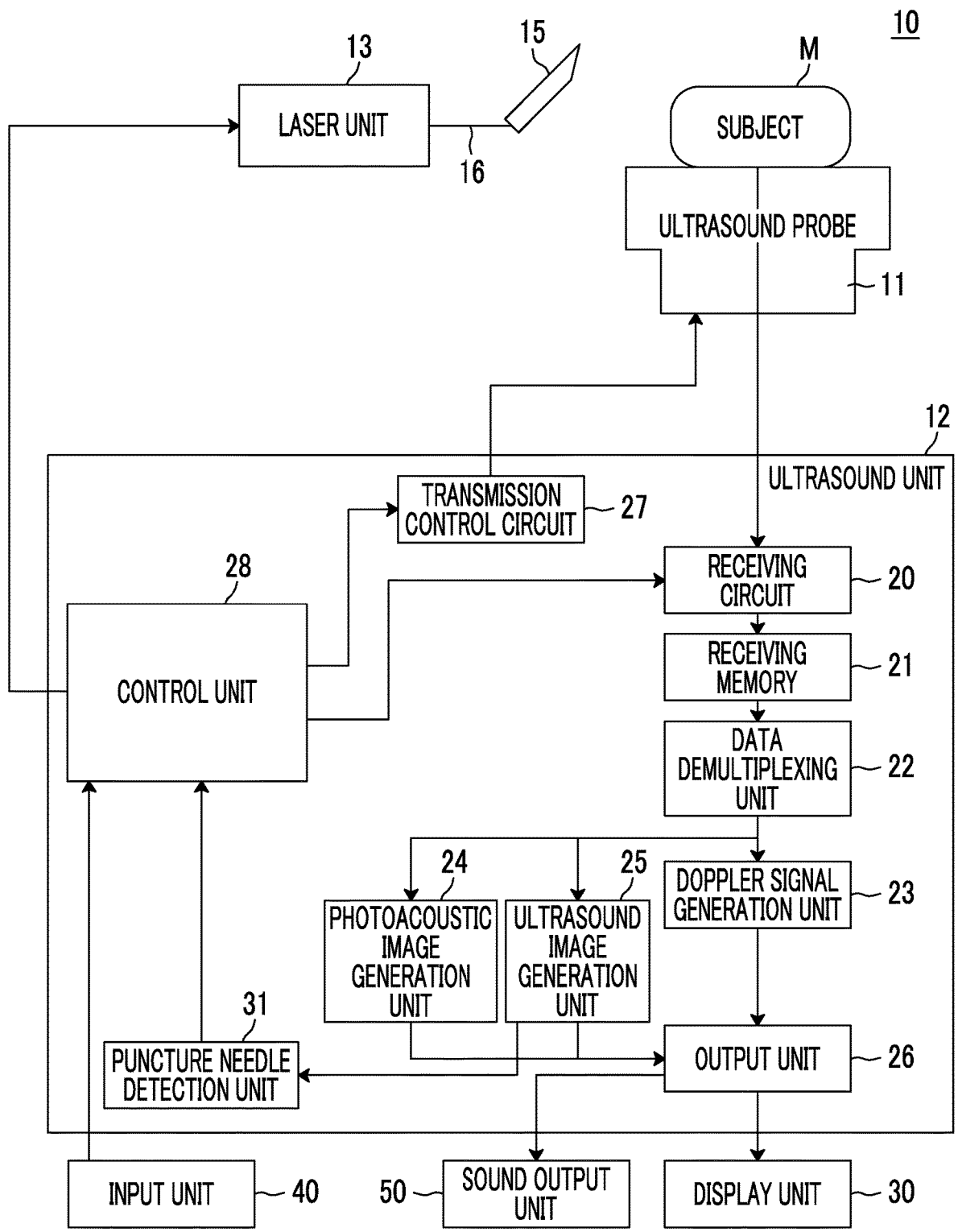
FIG. 10 is a block diagram schematically illustrating another embodiment of the photoacoustic measurement device according to the invention.

In the photoacoustic image generation apparatuses 10 according to the first and second embodiments, the waveform indicating a blood flow rate is displayed on the display unit 30 on the basis of the Doppler signal generated by the Doppler signal generation unit 23. However, the invention is not limited thereto. For example, sound information may be output on the basis of the Doppler signal. Specifically, for example, in the photoacoustic image generation apparatus 10 according to the first embodiment, as illustrated in FIG. 10, a sound output unit 50, such as a speaker device, may be provided and the output unit 26 directs the sound output unit 50 to output sound information on the basis of the Doppler signal.

Figure 11A:
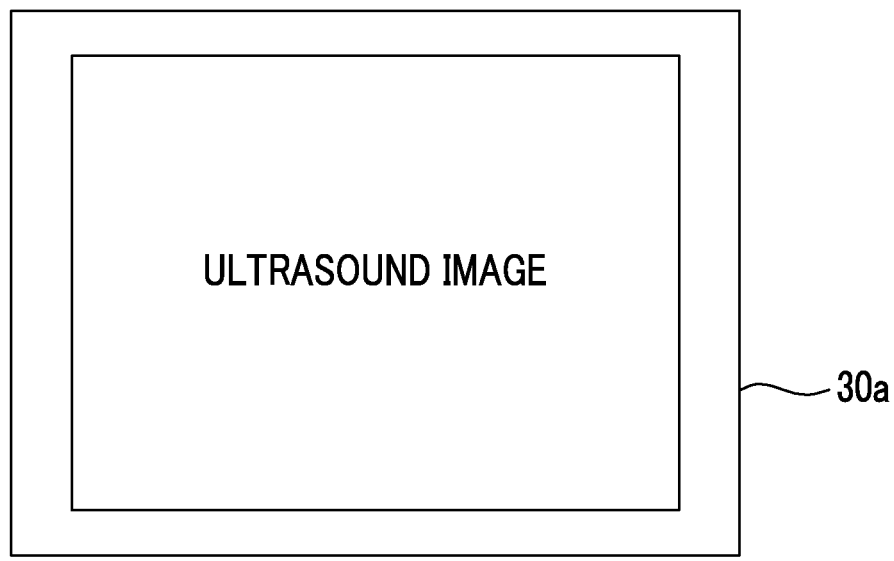
FIGS. 11A and 11B are diagrams illustrating examples of the display of an ultrasound image in a case in which sound information is output on the basis of a Doppler signal.
Figure 11B:
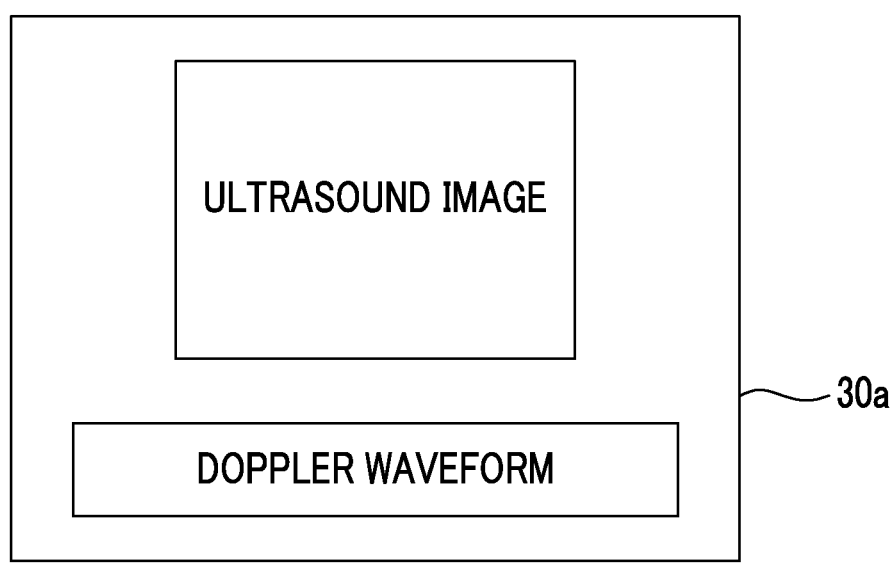

In a case in which the sound information is output from the sound output unit 50 on the basis of the Doppler signal as described above, an ultrasound image may be displayed on substantially the entire screen 30a of the display unit 30 and a Doppler waveform based on the Doppler signal may not be displayed as illustrated in FIG. 11A. Alternatively, a configuration may be used in which the user can select the full-screen display of an ultrasound image illustrated in FIG. 11A and the split-screen display of both a Doppler waveform and an ultrasound image illustrated in FIG. 11B.

In the second embodiment, the tip of the puncture needle 15 is located in the sample gate. However, the invention is not limited thereto. For example, the position of the sample gate may be set such that the distance of the tip of the puncture needle 15 from the sample gate is a predetermined distance.

In the above-described embodiments, the puncture needle 15 is used as an embodiment of the insert. However, the invention is not limited thereto. The insert may be a radio-frequency ablation needle including an electrode that is used for radio-frequency ablation, a catheter that is inserted into a blood vessel, or a guide wire for a catheter that is inserted into a blood vessel. Alternatively, the insert may be an optical fiber for laser treatment.

The insert according to the invention is not limited to a needle, such as an injection needle, and may be a biopsy needle used for biopsy. That is, the needle may be a biopsy needle that is inserted into an inspection target of the living body and extracts the tissues of a biopsy site of the inspection target. In this case, photoacoustic waves may be generated from an extraction portion (intake port) for sucking and extracting the tissues of the biopsy site. In addition, the needle may be used as a guiding needle that is used for insertion into a deep part, such as a part under the skin or an organ inside the abdomen.

In the above-described embodiments, a photoacoustic image is generated on the basis of the photoacoustic waves generated from the photoacoustic wave generation portion 15c. However, in the invention, imaging is not necessarily performed and the photoacoustic image may be generated in devices other than the photoacoustic measurement device.

The invention has been described above on the basis of the preferred embodiments. However, the insert and the photoacoustic measurement device according to the invention are not limited only to the above-described embodiments. Various modifications and changes of the configurations according to the above-described embodiments are also included in the scope of the invention.

EXPLANATION OF REFERENCES

10: photoacoustic image generation apparatus
11: ultrasound probe
12: ultrasound unit
13: laser unit
15: puncture needle
15a: puncture needle main body
15b: optical fiber
15c: photoacoustic wave generation portion
15d: hollow portion
16: optical cable
20: receiving circuit
21: receiving memory
22: data demultiplexing unit
23: Doppler signal generation unit
24: photoacoustic image generation unit
25: ultrasound image generation unit
26: output unit
27: transmission control circuit
28: control unit
29: tip position detection unit
30: display unit
30a: screen
31: puncture needle detection unit
40: input unit
50: sound output unit
C: center position
G: sample gate
L1, L2: straight line
M: subject
P: tip
Q: upper end of sample gate
R: lower end of sample gate
S: rectangular region
V: vertex
θ: angle
θth: threshold value

What is claimed is:

1. A photoacoustic measurement device comprising:
an insert of which at least a tip portion is configured to be inserted into a subject and which includes a light guide member that guides light to the tip portion and a photoacoustic wave generation portion that absorbs the light guided by the light guide member and generates photoacoustic waves;
an acoustic wave detection unit that detects the photoacoustic waves generated from the photoacoustic wave generation portion and detects reflected acoustic waves reflected by transmission of acoustic waves to the subject;
a processor configured to generate a Doppler signal on the basis of the reflected acoustic waves from a sample gate as a Doppler measurement target which have been detected by the acoustic wave detection unit, generate a reflected acoustic image on the basis of the reflected acoustic waves detected by the acoustic wave detection unit, and detect a length direction of the insert on the basis of the reflected acoustic image; and
a controller configured to control a steering direction of the sample gate on the basis of the length direction of the insert such that an angle θ formed between a straight line which extends in the length direction of the insert and a straight line which extends in the steering direction of the sample gate satisfies 0°≤θ≤45°.

2. The photoacoustic measurement device according to claim 1,
wherein the controller sets the steering direction of the sample gate, following a change in an insertion direction of the insert, in a state in which a magnitude of the angle θ is maintained.

3. The photoacoustic measurement device according to claim 1,
wherein the controller sets the angle θ to 0°.

4. The photoacoustic measurement device according to claim 1,
wherein the controller stores a plurality of steering angle candidates of the sample gate in advance and selects a steering angle, at which the angle θ satisfies 0°≤θ≤45° and the steering direction of the sample gate is closest to the length direction of the insert, from the plurality of steering angle candidates.

5. The photoacoustic measurement device according to claim 1, further comprising:
a photoacoustic image generation unit that generates a photoacoustic image on the basis of the photoacoustic waves detected by the acoustic wave detection unit;
wherein the processor is further configured to detect a position of the tip portion of the insert on the basis of the photoacoustic image,
wherein the controller controls a position of the sample gate such that the tip portion of the insert is included in the sample gate.

6. The photoacoustic measurement device according to claim 5,
wherein the controller controls the position of the sample gate such that a center position of the sample gate is matched with the tip portion of the insert.

7. The photoacoustic measurement device according to claim 5,
wherein the controller sets the position of the sample gate, following movement of the position of the tip portion of the insert, in a state in which a relative positional relationship between the position of the tip portion of the insert and the sample gate is maintained.

8. The photoacoustic measurement device according to claim 1,
wherein the processor detects the length direction of the insert at each interval of two or more frames of the reflected acoustic images.

9. The photoacoustic measurement device according to claim 8,
wherein the processor acquires an amount of change in an angle of the length direction of the insert, and
in a case in which the amount of change is equal to or less than a predetermined threshold value, the processor increases the frame interval at which the length direction of the insert is detected.

10. The photoacoustic measurement device according to claim 1, further comprising:
a photoacoustic image generation unit that generates a photoacoustic image on the basis of the photoacoustic waves detected by the acoustic wave detection unit;
wherein the processor is further configured to detect a position of the tip portion, of the insert on the basis of the photoacoustic image,
wherein, in a case in which the position of the tip portion of the insert that is detected is the same as a position of the tip portion of the insert in the photoacoustic image of a previous frame, the detection of the length direction of the insert based on the reflected acoustic image and the control of the steering direction of the sample gate based on the length direction of the insert are not performed.

11. The photoacoustic measurement device according to claim 1, wherein the processor is further configured to output sound information on the basis of the Doppler signal.

12. The photoacoustic measurement device according to claim 1,
wherein the insert is a needle that is configured to be inserted into the subject.

13. The photoacoustic measurement device according to claim 1, wherein the controller is further configured to:
determine whether the angle θ is greater than a predetermined threshold value;
based on the determination that the angle θ is greater than the predetermined threshold value, detect a position of the tip portion of the insert and set a position and steering direction of the sample gate on the basis of the length direction and the detected position of the tip portion of the puncture needle; and
based on the determination that the angle θ is not greater than the predetermined threshold value, detect the position of the tip portion of the insert and set the position and steering direction of the sample gate on the basis of the detected position of the tip portion of the puncture needle.

* * * * *